US008617808B2

(12) United States Patent
Braesch-Andersen et al.

(10) Patent No.: US 8,617,808 B2
(45) Date of Patent: *Dec. 31, 2013

(54) CULTISPOT ASSAY

(75) Inventors: Sten Braesch-Andersen, Nacka Strand (SE); Staffan Paulie, Nacka Strand (SE)

(73) Assignee: Mabtech AB, Nacka Strand (SE)

( * ) Notice: Subject to any disclaimer, the term of this patent is extended or adjusted under 35 U.S.C. 154(b) by 724 days.

This patent is subject to a terminal disclaimer.

(21) Appl. No.: 11/587,350

(22) PCT Filed: Apr. 29, 2005

(86) PCT No.: PCT/EP2005/004621
§ 371 (c)(1),
(2), (4) Date: Dec. 20, 2006

(87) PCT Pub. No.: WO2005/106482
PCT Pub. Date: Nov. 10, 2005

(65) Prior Publication Data
US 2007/0178449 A1    Aug. 2, 2007

(30) Foreign Application Priority Data

Apr. 30, 2004    (GB) .................................. 0409771.3

(51) Int. Cl.
| C12Q 1/68 | (2006.01) |
|---|---|
| C12Q 1/70 | (2006.01) |
| A61K 49/00 | (2006.01) |
| A61K 39/00 | (2006.01) |
| A61K 39/395 | (2006.01) |
| A61K 39/42 | (2006.01) |

(52) U.S. Cl.
USPC .............. 435/6.1; 435/5; 424/9.1; 424/141.1; 424/139.1; 424/147.1; 424/159.1

(58) Field of Classification Search
None
See application file for complete search history.

(56) References Cited

U.S. PATENT DOCUMENTS

| 4,591,570 | A | * | 5/1986 | Chang ........................... 435/7.24 |
|---|---|---|---|---|
| 5,432,099 | A | | 7/1995 | Ekins |
| 6,410,252 | B1 | | 6/2002 | Lehmann et al. |
| 2003/0021766 | A1 | | 1/2003 | Vajdy et al. |
| 2004/0049351 | A1 | | 3/2004 | Matson et al. |
| 2006/0079461 | A1 | * | 4/2006 | Brewer et al. .................... 514/18 |
| 2008/0145837 | A1 | * | 6/2008 | Paulie et al. ........................ 435/5 |

FOREIGN PATENT DOCUMENTS

| EP | 0 063 810 A1 | 11/1982 |
|---|---|---|
| EP | 0 957 359 A2 | 11/1999 |
| JP | 6-502726 | 3/1994 |
| WO | WO 84/03151 A1 | 8/1984 |
| WO | WO 90/04182 | 4/1990 |
| WO | WO 01/27611 A3 | 4/2001 |
| WO | WO 02/073195 A2 | 9/2002 |
| WO | WO 03/023360 A2 | 3/2003 |
| WO | WO 03/038062 A3 | 5/2003 |
| WO | WO 2005/106479 A1 | 11/2005 |

OTHER PUBLICATIONS

Hassan et al., Expression of a unique protein on colon cancer cells that reacts with a novel monoclonal antibody and ulcerative colitis serum, 1995, Clinical Experimental Immunology, vol. 100 pp. 457-462.*

Helms et al., Direct Visualization of Cytokine-Producing Recall Antigen-Specific CD4 Memory T Cells in Healthy Individuals and HIV Patients, 2000, The Journal of Immunology, vol. 164, pp. 3723-3732.*

Huang et al., Enhanced Protein Profiling Arrays with ELISA-Based Amplification for High-Throughput Molecular Changes of Tumor Patients' Plasma, 2004, Clinical Cancer Research, vol. 10, pp. 598-609.*

Nicolaieff et al., Detection of Rotavirus by Serological Trapping on Antibody-Coated Electron Microscope Grids, 1980, Journal of Clinical Microbiology, vol. 12, No. 1, pp. 101-104.*

Chen, Y. and Peng, Z., "A Sensitive In Situ Elisa for Quantitative Measurements of Cytokines and Antibodies Secreted by Culture Lymphocytes," *Journal of Immunoassay & Immunochemistry*, 22(4):353-369 (2001).

Corne, P., et al., "Detection and Enumeration of HIV-1-Producing Cells by ELISPOT (Enzyme-Linked ImmunoSpot) Assay," *Journal of Acquired Immune Deficiency Syndromes and Human Retrovirology*, 20:442-447, (1999).

Culshaw, R.J., et al., "Gut Intraepithelial Lymphocytes Induce Immunity Against Cryptosporidium Infection Through a Mechanism Involving Gamma Interferon Production," *Infection and Immunity*, 65(8):3074-3079, (1997).

Czerkinsky, C.C., et al., "An Immunoenzyme Procedure for Enumerating Fibronectin-Secreting Cells," *Journal of Immunoassay*, 5(3 &4): 291-302, (1984).

Ekins, R.P. and Chu, F., "Developing Multianalyte Assays," *Tibtech*, 12:89-94, (1994).

Gazagne, A., et al., "A Fluorospot Assay to Detect Single T Lymphocytes Simultaneously Producing Multiple Cytokines," *Journal of Immunological Methods*, 283:91-98, (2003).

Geppert, T.D. and Lipsky, P.E., "Accessory Cell Independent Proliferation of Human T4 Cells Stimulated by Immobilized Monoclonal Antibodies to CD3," *The Journal of Immunology*, 138(6): 1660-1666, (1987).

(Continued)

*Primary Examiner* — Benjamin P Blumel
(74) *Attorney, Agent, or Firm* — Hamilton, Brook, Smith & Reynolds, P.C.

(57) ABSTRACT

The invention provides a method for detecting the production of one or more analytes by cells in a sample. The method uses one or more immobilized binding proteins to capture one or more analytes released from cells. The, or each, binding protein is localized at one or more discrete locations on a solid surface within a well. Cells are introduced into the well and cultured under conditions suitable for release of the analyte(s) and for binding of the analyte(s) to the binding protein(s). Restricting the binding protein(s) to one or more discrete locations within the well, rather than coating the entire surface of the well, results in increased sensitivity of the assay.

18 Claims, 2 Drawing Sheets

(56) References Cited

OTHER PUBLICATIONS

Hagiwara, E., et al., "Phenotype and Frequency of Cells Secreting IL-2, IL-4, IL-6, IL-10, IFN and TNF-α in Human Peripheral Blood," *Cytokine*, 7(8):815-822, (1995).

Jansson, A., et al., "Elispot Assay Detection of Cytokine Secretion in Multiple Sclerosis Patients Treated With Interferon-β 1a or Glatiramer Acetate Compared With Untreated Patients," *Multiple Sclerosis*, 9:440-445, (2003).

Jennes, W., et al., "Enhanced ELISPOT Detection of Antigen-Specific T Cell Responses From Cryopreserved Specimens With Addition of Both IL-7 and IL-15—The Amplispot Assay," *Journal of Immunological Methods*, 270:99-108, (2002).

Kouwenhoven, M., et al., "Enzyme-Linked Immunospot Assays Provide a Sensitive Tool for Detection of Cytokine Secretion by Monocytes," *Clinical and Diagnostic Laboratory Immunology*, 8(6):1248-1257, (2001).

Mäkitalo, B., et al., "ELISpot and ELISA Analysis of Spontaneous, Mitogen-Induced and Antigen-Specific Cytokine Production in Cynomolgus and *Rhesus macaques*," *Journal of Immunological Methods*, 270:85-97, (2002).

Moldovan, I.R., et al., "Interferon Gamma Responses to Myelin Peptides in Multiple Sclerosis Correlate With a New Clinical Measure of Disease Progression," *Journal of Neuroimmunology*, 141:132-140, (2003).

Okamoto, Y., et al., "Development of a Dual Color Enzyme-Linked Immunospot Assay for Simultaneous Detection of Murine T Helper Type 1- and T Helper Type 2-Cells," *Immunopharmacology*, 39:107-116, (1998).

Ott, P.A., et al., "CD28 Costimulation Enhances the Sensitivity of the ELISPOT Assay for Detection of Antigen-Specific Memory Effector CD4 and CD8 Cell Populations in Human Diseases," *Journal of Immunological Methods*, 285:223-235, (2004).

Westermann, J., et al., "T Cell Reactivity Against bcr/abl Fusion Peptides in Healthy Donors and CML Patients," *Biology and Genetics*, p. 1 of 1, XP008052088. (2002).

Van Emmerik, N.E.M., et al., "The Avidity of Allospecific Cytotoxic T Lymphocytes (CTL) Determines Their Cytokine Production Profile," *Clinical and Experimental Immunology*, 110:447-453, (1997).

Westermann, J., et al., "T Cell Reactivity Against bcr/abl Fusion Peptides in Healthy Donors and CML Patients", [online], Chemical Abstracts Service, (Dec. 2002).

R&D Systems, Mouse IFN-γ Development Module product information sheet, Catalog No. SEL485, 2008.

Notification of Transmittal of the International Search Report and the Written Opinion of the International Searching Authority, or the Declaration, International Search Report and the Written Opinion in PCT Application No. PCT/EP2005/004620, 14 pages, mailed Sep. 26, 2005.

Notification Concerning Transmittal of International Preliminary Report on Patentability and International Preliminary Report on Patentability in International Application No. PCT/EP2005/004620, 9 pages, mailed Nov. 9, 2006.

Crotty, et al., "Tracking human antigen-specific memory B cells: a sensitive and generalized ELISPOT system," *J. of Immunological Methods*, 286: 111-122 (2004).

Okamoto, et al., "Cytokine Balance in the Pathogenesis of Rheumatoid Arthritis," *Yakugaku Zasshi*, 121(2): 131-138 (2001).

Notification Concerning Transmittal of International Preliminary Report on Patentability and International Preliminary Report on Patentability in International Application No. PCT/EP2005/004621, 7 pages, date of mailing Nov. 9, 2006.

Butler, J.E., "Solid Supports in Enzyme-Linked Immunosorbent Assay and Other Solid-Phase Immunoassays," *Methods*, 22:4-23 (2000).

Chapoval, S.P., et al., "Allergic Inflammatory Response to Short Ragweed Allergenic Extract in HLA-DQ Transgenic Mice Lacking CD4 Gene." The American Association of Immunologists, vol. 168, pp. 890-899, (2002).

\* cited by examiner

CULTISPOT ASSAY

RELATED APPLICATIONS

This application is the U.S. National Stage of International Application No. PCT/EP2005/004621, filed Apr. 29, 2005, published in English, and claims priority under 35 U.S.C. §119 or 365 to UK Application No. 0409771.3 filed Apr. 30, 2004.

FIELD OF THE INVENTION

The invention relates to a method for detecting the production of one or more analytes by cells. The invention also relates to a novel product for use in a method of detecting the production of one or more analytes by cells, a kit comprising the product, uses of the product and kit and a method for producing the product.

BACKGROUND TO THE INVENTION

Assays used for the detection of secreted cytokines as well as other soluble substances at the protein level include the ELISA and ELISpot assays. For example, the enzyme-linked immunospot assay (ELISpot) is widely used for the detection of T-cell specific responses. In the ELISpot assay, T-cells secreting a specific cytokine are detected by incubating the T-cells in an ELISpot assay plate on which antibodies specific for the cytokine are immobilised. Cytokine bound to the antibodies is then visualised using standard immunoassay procedures. Spots of bound cytokine localised in areas of the assay plate where cytokine production has occurred indicate the presence of activated T-cells. Each spot represents cytokine production by a single cell. Therefore, if the number of cells present in the assay is known, the ELISpot assay allows the frequency of responding cell to be ascertained by counting the number of spots formed.

The ELISpot assay has also been used for other purposes such as the detection of virus infected cells, the enumeration of cells secreting specific antibody, the detection of the cells secreting fibronectin and the study of monocytes.

The use of soluble cofactors to enhance the detection of positive cells in the ELISpot assay has been described. Immobilised cofactors have been used to stimulate T-cells and the presence of cytokines in the culture medium has been detected by ELISA-based analysis.

The ELISpot assay is ideal for analytes involving low numbers of responding or producing cells. A good example of this is the analysis of specific immune response which typically involve less than 0.1% responding cells. However, the ELISpot assay has the limitation that the number of cells in an individual sample must be restricted so that only a monolayer of cells is present in the assay well (approximately 250,000 cells/well in a 96 well plate).

The ELISA assay enables the amount of cytokine produced to be quantitated. However, the ELISA assay is not useful for analytes, such as analysis of a specific immune response, where only a few cells produce the protein being detected due to its low sensitivity.

SUMMARY OF THE INVENTION

The present invention provides a novel assay which combines the advantages of ELISpot with the simultaneous cultivation of cells and capture of cellular products with the flexibility of antibody assays and so provides a highly sensitive means for the in vitro detection of products released by cultured cells. The assay of the invention utilises an assay plate on which antibodies to one or more analytes are immobilised at discrete locations on a solid surface. The novel assay of the invention allows the simultaneous detection of multiple cytokines released by cultured cells in an individual sample. The assay of the invention is very sensitive and so may be used for analytes involving low numbers of responding or producing cells, such as in the analysis of specific immune responses. Unlike the ELISpot assay, the number of cells that may be present in an individual sample is not restricted. Therefore, a larger number of cells may be assayed per well in the assay of the invention. Accordingly, sensitivity of the novel assay is increased compared to the known ELISpot assay.

The assay of the invention is thus highly sensitive and enables the analysis of more than one parameter in the same assay well with the same sample of cells. The assay of the invention is particularly useful in diagnostic applications where only a positive or negative result is required. For example, the assay may be used to determine whether an individual has been exposed to and is capable of responding to an infectious agent, or in the detection of virus infected cells.

Accordingly, the present invention provides a method for detecting the production by cells in a sample of one or more analyte, which method comprises:
(a) providing
   (i) a first binding protein which specifically binds to a first analyte; and
   (ii) optionally a second binding protein which specifically binds to a second analyte;
wherein said first binding protein and optionally said second binding protein are each immobilized at one or more discrete location within a well;
(b) introducing a sample of cells into said well;
(c) culturing said sample of cells under conditions suitable for:
   (i) release of said first analyte and optionally said second analyte and optionally said one or more further analyte by said cells; and
   (ii) binding of said first analyte to said first binding protein and optionally binding of said second analyte to said second binding protein; and
(d) determining whether or not said first analyte is bound to said first binding protein and whether or not said second analyte is bound to said second binding protein,
thereby detecting production by a sample of cells of one or more analyte.

Figure 1:
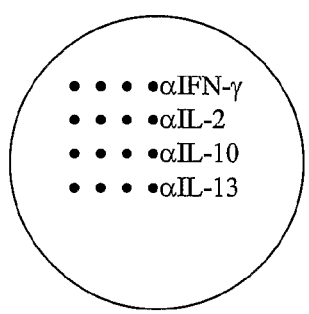
FIG. 1 shows the results of an experiment to test the specificity of the system. Four different anti-cytokine catcher antibodies, αIFN-γ, αIL-2, αIL-10 and αIL-13, were added onto PVDF plates according to the pattern shown in FIG. 1 (4 nl/spot). 100 µl/well of a solution containing no cytokines (control well 1), 5 ng/ml each of purified αIFN-γ, αIL-2, αIL-10 and αIL-13 (well 2) or 5 ng/ml of one of purified αIFN-γ, αIL-2, αIL-10 and αIL-13 (wells 3 to 6).
Figure 1:
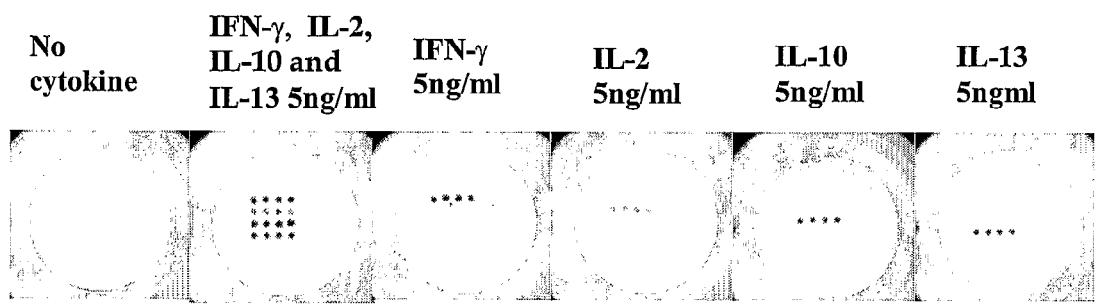
Figure 2:
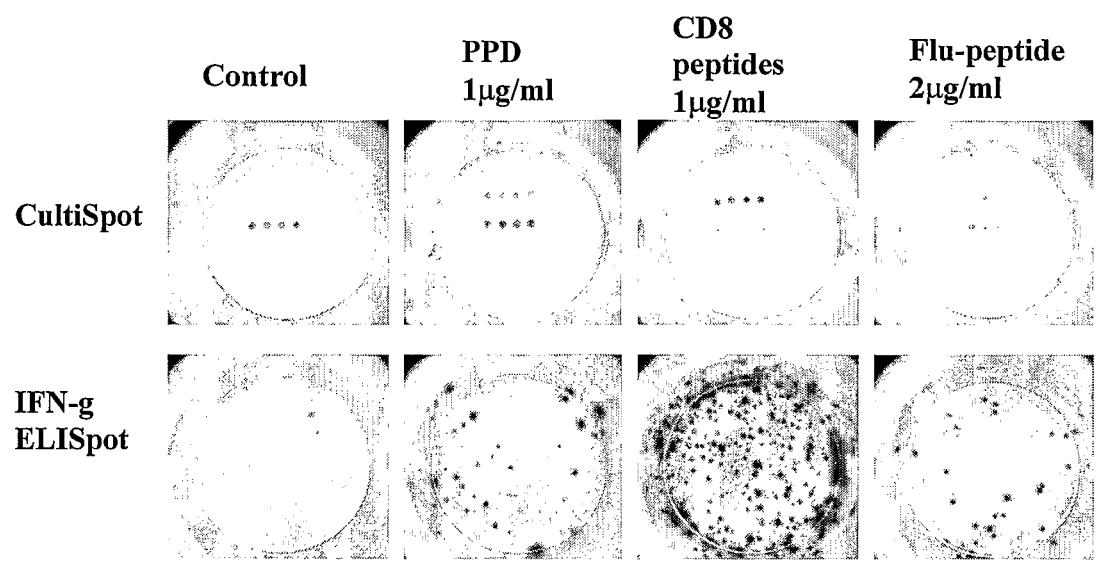
FIG. 2 is a comparison of the novel assay of the invention (Cultispot) and the ELISpot assay. The top panel shows the detection of cytokines produced by PBMC in response to different stimuli using a PVDF plate prepared as described for FIG. 1. The bottom panel shows the detection by ELISpot of IFN-γ produced by PBMC in response to different stimuli using a PVDF plate uniformly coated with an anti-IFN-γ catcher antibody. PBMC (180 000/well) were cultured at 37°

C. for 44 hours in the presence of PPD (purified protein derivative from mycobacterium), a pool of CD8-reactive viral peptides, flu-peptide (a single peptide from the influenza virus) or medium alone.

DETAILED DESCRIPTION OF THE INVENTION

The present invention provides an in vitro method for detecting the production of one or more analyte by a sample of cells, which method comprises:
(a) providing
  (i) a first binding protein which specifically binds to a first analyte; and
  (ii) optionally a second binding protein which specifically binds to a second analyte;
  wherein said first binding protein and optionally said second binding protein are each immobilized at one or more discrete location within a well;
(b) introducing a sample of cells into said well;
(c) culturing said sample of cells under conditions suitable for:
  (i) release of said first analyte and optionally said second analyte by said cells; and
  (ii) binding of said first analyte to said first binding protein and optionally binding of said second analyte to said second binding protein; and
(d) determining whether or not said first analyte is bound to said first binding protein and optionally whether or not said second analyte is bound to said second binding protein,
thereby detecting production by a sample of cells of one or more analyte.

One or more further binding proteins may also be present in the well at one or more discrete location. Each further binding protein is typically present at a different discrete location within the well. Each further binding protein specifically binds to one further analyte. Where one or more further binding protein is present on said solid surface, step (c) additionally comprises culturing the cells under conditions suitable for:
  (iii) release of each one or more further analyte by the cells; and
  (iv) binding of each further analyte to each one or more further binding protein;
and step (d) additionally comprises determining whether or not each of said one or more further analytes is bound to each of the further binding proteins.

From 0 to 60, for example from 2 to 50, 3 to 40, 4 to 30, 5 to 20, 6 to 18, 7 to 15, 8 to 12 or 9 to 10 further binding proteins may be present within the well.

Binding Protein

The first binding protein is a protein capable of specifically binding to a first analyte. The second binding protein is a protein capable of specifically binding to a second analyte. A further binding protein is capable of specifically binding to a further analyte. A protein "specifically binds" to an analyte when it binds with preferential or high affinity to the analyte for which it is specific but does not bind, does not substantially bind or binds with only low affinity to other substances. The specific binding capability of a protein may be determined by any suitable method. A variety of protocols for competitive binding are well known in the art (see, for example, Maddox et al. (1993), J. Exp. Med. 158:1211-1226).

Preferably, one or more of the first, second and further binding proteins is an antibody. The antibody may be a monoclonal or polyclonal antibody. Monoclonal antibodies are preferred. The binding proteins may also be, or comprise, an affinity ligand or an antibody fragment, which fragment is capable of binding to the analyte. Such antibody fragments include Fv, F(ab') and F(ab')$_2$ fragments as well as single chain antibodies. Preferably, the first, second and each of the further binding proteins are antibodies or antibody fragments.

In one embodiment, the invention provides a method of detecting T-cells which secrete a cytokine in response to a stimulatory agent. In this embodiment, an antibody suitable for use in the method of the invention typically binds specifically to one or more cytokines, for example to two, three or four cytokines but preferably to one cytokine. Preferably the antibody binds specifically to IFN-γ or IL-4. Antibodies to cytokines are commercially available, or can be made using standard techniques. Commercially available antibodies include the following monoclonal antibodies from Mabtech AB, Stockholm, Sweden: IL2-I and IL2-II for IL-2, 82.4 and 12.1 or IL4-I and IL4-II for IL-4, TRFK5 and 5A10 for IL-5, IL13-I and IL13-2 for IL-13, 1-D1K and 7-B6-1 for IFN-γ, 13A5 and 39C3 for IL-6, 9D7 and 12G8 for IL-10, IL-12-I, IL-12-II and IL-12-III for IL-12, TNFα-I and TNFα-II for TNF-α, pf-344 for perforin and IFNα-I and IFNα-II for IFNα.

Analyte

The analyte for detection in the method of the invention may be any substance produced by a cell. In general, the analyte is a protein. The analyte is typically secreted from the cells. It is preferred that the analyte is an immunoreactive substance, i.e. a substance which binds to an antibody. A method of the invention may be used to detect one or more, for example from 2 to 100, 3 to 75, 4 to 60, 5 to 50, 6 to 40, 7 to 30, 8 to 20, 9 to 15 or 10 to 12 analytes produced by a single sample of cells.

In the preferred embodiment where the cells are T-cells, the analyte is typically a cytokine. The cytokine may be selected from an interleukin, preferably IFN-1, IL-2, IL-4, IL-5, IL-6, IL-10, IL-12 or IL-13, an interferon, preferably IL-γ or other cytokines such as TNF-α. More preferably, the cytokine is IFN-γ or IL-4. Preferably the cytokine is released when the T-cell is contacted with a stimulatory substance such as an antigen or allergen. Preferred combinations of cytokines for simultaneous detection include IFN-γ and any one or more IL-2, IL-4, IL-5 and IL-10.

In the preferred embodiment where the cells are virus infected cells, the analytes are typically virus particles or virus proteins. Where the cells are cancer cells, the analytes are typically growth factors or growth regulatory proteins. Where the cells are parasite infected cells, such as parasite infected blood cells, the analytes are typically parasite derived proteins.

Well

The well is typically a well of a multi-well plate. The binding proteins are typically immobilized on the base of the well. A well is any structure suitable for holding a solution, which comprises a solid surface on which the binding protein may be immobilised and which is suitable for detecting binding of an analyte to a binding protein immobilised on the surface. The well typically comprises a flat horizontal base and a vertical wall or walls. The well typically has a capacity of from about 25 µl to about 250 µl, from about 30 µl to about 200 µl, from about 40 µl to about 150 µl or from about 50 to 100 µl. It is not essential that the solid surface is the base of the well provided that the surface is capable of being brought into contact with a sample of cells under suitable culture conditions. For example, the binding reagents may be immobilized on a solid surface such as a coverslip or similar which is placed in the well during cell culture.

The area of the solid surface on which the binding proteins are immobilised is typically from about 0.05 cm² to about 1 cm², for example from about 0.2 cm² to about 0.5 cm² or from about 0.3 cm² to about 0.4 cm².

In a preferred format, the well is a single well of a multi-well plate, for example a 96 well plate. Suitable 96 well plates are commonly used in ELISA and ELISpot assays.

In the assay of the invention, more than one analyte produced by cells may be detected in a single well of a multi-well plate. Separate assays may be carried out in separate wells in the plate.

Preferably the binding proteins are immobilized is a polyvinylidene fluoride (PVDF)-membrane or a nitrocellulose-membrane. Other membranes with similar high protein binding capacities to PVDF and nitrocellulose-membranes may also be used. Typically, the surface to which the binding proteins are immobilized has a protein binding capacity of from about 50 to about 100 µg per well of a 96-well plate, such as about 60, about 70, about 80 or about 90 kg per well. The surface area of a 96-well ELISpot place is about 0.32 cm². Accordingly, the solid surface has a protein binding capacity of from about 150 µg per cm² to 350 µg per cm², such as 180 µg per cm², 200 µg per cm², 250 µg per cm² or 300 µg per cm².

The first binding protein is immobilized at one or more discrete location within the well, or on the solid surface placed within the well. A discrete location is typically an area or region of the surface, or well, which has a small surface area in relation to the total surface area of the solid surface, or well. The surface area of the discrete location may be from about 1/200 to about 1/2 of the total surface area, for example from about 1/100 to about 1/3, about 1/50 to about 1/4, about 1/20 to about 1/8 or about 1/15 to about 1/10 of the total surface area.

The discrete location typically comprises a spot. The spot has a typical diameter of from about 1 nm to about 200 µm, for example from about 1 µm to about 100 µm or from about 10 µm to about 50 µm. From 2 to 50, from 3 to 40, from 4 to 30, from 5 to 20, from 6 to 15, from 7 to 12, 8, 9 or 10 spots of immobilized binding proteins may be present within the well.

The spots may be arranged in any suitable array on the surface provided that the spots are separated from one another. The spots are typically arranged in one or more straight lines to aid identification of spots to which the first, second or further analyte has bound. For example, the spots may be arranged as a grid. In a grid, the first binding protein may be present in one row or column and the second binding protein in a second row or column. One or more further binding protein may be present in additional spots which may form additional rows or columns in the grid. Alternatively, the spots may form a circular array.

The first, second and further binding proteins are may be located at discrete locations on a protein chip or other solid surface, instead of in a well, provided that the first, second and further binding proteins are located such that a single sample of cells may simultaneously contact each of the binding proteins on the solid surface.

Cells

Any cells which produce an analyte which may be detected using a specific binding protein may be used in the assay. In one preferred embodiment, the sample of cells comprises T-cells. The T-cells are generally taken from a subject in a blood sample, although other types of samples which contain T-cells can be used. The sample may be added directly to the assay or may be processed. Typically, the processing may comprise the isolation of cells from the blood and the suspension of these in cell culture medium or buffer. The cell suspension may be diluted to contain different concentrations of cells depending on the test situation. The concentration of cells in the sample may be higher than that in blood.

Preferably, the T-cells used in the assay are in the form of unprocessed or diluted samples. The T-cells may be freshly isolated (e.g. freshly isolated mononuclear cells (MNCs)) or peripheral blood mononuclear cells (PBMCs) which are used directly ex vivo, i.e. they are not cultured before being used in the method. Alternatively, the T-cells may have been cultured in vitro prior to use in the assay.

In a second preferred embodiment, the cells may be virus-infected cells. The cells may be blood cells, for example lymphocytes, monocytes or granulocytes. Other suitable cells may be isolated from urine, saliva, semen or vaginal secretions. Other cell types may also be screened, depending on the trophism of the virus. Virus infected cells that may be detected by a method of the invention include cells infected with human immunodeficiency virus (HIV), Epstein Barr virus (EBV) and cytomegalovirus (CMV).

A variety of other cells, including cancer cells, neural cells and stem cells may also be used in an assay of the invention.

Generally from about $10^4$ to about $10^7$ cells are present in the sample. For example, from about $2.5 \times 10^4$, about $2.5 \times 10^6$, about $5 \times 10^5$, about $10^5$ to about $3 \times 10^5$, about $3 \times 10^5$ to about $10^6$ cells may be present in the sample.

Culture Conditions

In a method of the invention, the sample of cells is introduced into the well or brought into contact with the immobilized binding proteins under any conditions suitable for release of first analyte, and optionally the second or further analyte from the cells. The conditions are also suitable for the analyte(s) to bind to the immobilised binding protein(s). Generally, the cells will be present in a solution which is preferably culture medium.

The assay may be carried out in any suitable volume. Typical volumes of the cell sample range from about 10 µl to about 1 ml, preferably from about 50 µl to about 500 µl, more preferably from about 100 µl to about 200 µl. Typically, the length of time for which the cells are incubated with the solid surface is from about 4 to about 50 hours, for example from about 6 to about 48 hours from about 8 to about 45 hours, from about 12 to about 36 hours or from about 16 to about 32 hours, preferably from about 6 to about 16 hours, for example overnight.

The cells may be incubated at any suitable temperature. The suitable temperature is in the same range as the normal body temperature of the human or animal from which the cells are derived. Typically, the incubation is carried out at a temperature between about 35° C. and about 39° C., preferably from about 36° C. to about 38° C., more preferably at 37° C.

Determining Binding

The complex formed between the immobilised binding protein and analyte released from the cells may be detected by any suitable means. The surface to which the antibody is immobilised is generally washed, for example in PBS, to remove unbound immunoreactive substance prior to detection.

Typically the binding protein/analyte complex may be detected using an antibody which will bind to the complex. Where the binding protein is an antibody, the second antibody is typically a different antibody to the binding protein. Typically, the antibody binds the analyte at a site which is different to the site which binds the binding protein. The antibody may be specific for the complex formed between the analyte and the binding protein immobilised on the solid support.

Generally, the second antibody is labelled with a label that may be detected either directly or indirectly. A directly detectable label may comprise a fluorescent label such as fluorescein, Texas red, rhodamine or Oregon green. The binding of a fluorescently labelled antibody to the immobilised binding protein/analyte complex may be detected by microscopy. For example, using a fluorescent or bifocal microscope.

Preferably, the antibody is conjugated to a label that may be detected indirectly. The label that may be detected indirectly may comprise an enzyme which acts on a precipitating non-fluorescent substrate that can be detected under a conventional low-magnifying, for example 10 times magnification, 20 times magnification or 50 times magnification, microscope such as a stereomicroscope or using an automated ELISpot reader. A magnifying glass may alternatively be used to distinguish the spots. An automated ELISpot reader is typically based on a video camera and image analysis software adapted for the analysis of spots. Preferred enzymes include alkaline phosphatase and horseradish peroxidase.

Other indirect methods may be used to enhance the signal from the second antibody or binding protein. For example, the second antibody or binding protein may be biotinylated allowing detection using streptavidin conjugated to an enzyme such as alkaline phosphatase or horseradish peroxidase or streptavidin conjugated to a fluorescent probe such as FITC or Texas red.

In all detection steps, it is desirable to include an agent to minimise non-specific binding of the second and subsequent agent. For example bovine serum albumin (BSA) or foetal calf serum (FCS) may be used to block non-specific binding.

The analyte released from the cells in response to a first agent may also be released spontaneously from the cells in the absence of the agent. Therefore, it may be necessary to carry out one or more negative control assays to determine whether or not the cells are releasing the analyte in response to the first agent. For example, the assay may be carried out in the absence of the stimulatory agent and the signal detected in the absence of the first agent may compared to the signal detected in the presence of the first agent.

First Agent

The method of the invention is typically used to detect cells which produce an analyte in response to a specific stimulatory signal. Accordingly, the cells being tested may be contacted with a first agent capable of stimulating secretion of the analyte.

In a method of the invention, the sample of cells may be cultured in step (c) with a first agent capable of inducing or inhibiting production of the first and/or second analyte and/or one or more of the further analytes. In the embodiment where the cells are T-cells it is preferred that a first agent capable of stimulating secretion is added to the assay wells, i.e. that the T-cells are cultured in the presence of the first agent.

Thus, step (b) of the method of the invention may further comprise contacting the sample of cells with a first agent capable of inducing or inhibiting production of first and/or second analyte and/or one or more of the further analytes.

The agent capable of inducing or stimulating production or secretion of the analyte may be present in solution or immobilised on the support. Where the first agent is immobilized on the surface, it may be present across the whole surface. Alternatively, the first agent may be located on a part of the support where no binding proteins are located, preferably at a discrete location.

In the embodiment where the method is for detecting activated T-cells, the agent capable of stimulating secretion is typically an antigen. The antigen may be from a pathogen such as a virus or bacteria. The antigen may be associated with an autoimmune disorder, such as autoimmune neurological disorders (myelin) or diabetes (glutamic acid decarboxylase (GAD)). The antigen may be a tumour antigen or an allergen. The agent capable of stimulating secretion may comprise a crude antigenic mixture isolated or recombinantly produced protein(s) and/or manufactured peptides.

The method of the invention may be used to detect cells which produce or secrete one or more analyte either spontaneously or in response to a stimulatory signal. The method of the invention may also be used to identify an agent which inhibits production or secretion of the analyte. Such an agent may inhibit the spontaneous secretion of the analyte or may inhibit secretion of the analyte in response to a specific stimulus.

For example, in the embodiment of the invention for detecting virus infected cells, the method may be used to identify anti-viral drugs. In such a method of drug screening, the method of the invention may be carried out in the presence and absence of the agent being tested and any decrease in the number of cells secreting a viral protein or particle in the presence of the test agent indicates that the agent may be useful as an anti-viral drug. Accordingly, the present invention provides a method for determining whether a test agent has antiviral activity, which method comprises:

(a) providing
  (i) a first binding protein which specifically binds to a first viral protein; and
  (ii) optionally a second binding protein which specifically binds to a second viral protein;
wherein said first binding protein and optionally said second binding protein are each immobilized at one or more discrete location on a solid surface;
(b) contacting said solid surface with a sample of virus infected cells and a test agent;
(c) culturing said sample of cells under conditions suitable for:
  (i) release of said first viral protein and optionally said second viral protein by said cells; and
  (ii) binding of said first viral protein to said first binding protein and optionally binding of said second viral protein to said second binding protein; and
(d) determining whether or not said first viral protein is bound to said first binding protein and optionally whether or not said second viral protein is bound to said second binding protein,
thereby determining whether said test agent has antiviral activity.

In the embodiment for detecting T-cells, the method may be used to identify immunoregulatory agents, for example in an antigen-specific system. The immunoregulatory agents may be suppressive or potentiating. In such a method of screening, the method of the invention may be carried out in the presence and absence of the test agent and any increase or decrease in the number of cells secreting a cytokine in the presence of the test agent indicates that the agent has immunoregulatory activity. Thus, the present invention provides a method for determining whether a test agent has immunoregulatory activity, which method comprises:

(a) providing
  (i) a first binding protein which specifically binds to a first cytokine; and
  (i) optionally a second binding protein which specifically binds to a second cytokine;
wherein said first binding protein and optionally said second binding protein are each immobilized at one or more discrete location on a solid surface;
(b) contacting said solid surface with a sample of T-cells and a test agent;

(c) culturing said sample of cells under conditions suitable for:
  (i) release of said first cytokine and optionally said second cytokine; and
  (ii) binding of said first cytokine to said first binding protein and optionally binding of said second cytokine to said second binding protein; and
(d) determining whether or not said first cytokine is bound to said first binding protein and optionally whether or not said second cytokine is bound to said second binding protein,
thereby determining whether said test agent has immunoregulatory activity.

The cells may be incubated with the test agent prior to contacting the cells with the antibody and agent capable of enhancing detection. Alternatively, the test agent may be contacted with the cells at the same time as the cells are brought into contact with the antibody and agent capable of enhancing detection.

Second Agent

In a method of the invention, the sample of cells may also be contacted with a second agent which enhances detection of one or more of the first, second and further analytes. The second agent may be added in solution during step (b) or may be immobilized on the solid surface. Where the second agent is immoblised on the surface, it may be present across the whole solid surface on which the first and optionally second and further binding proteins are immoblised. Alternatively the second agent may be present on a part of the support not containing a binding protein, preferably at a discrete location.

The second agent capable of enhancing detection of the first, second and/or further analyte may be a substance that enhances the production or secretion of said analyte.

Such second agents are also useful as positive controls. In this aspect, one or more but not all of the wells in a microtiter plate may contain the second agent or the second agent may be added in solution to one or more but not all of the wells of the assay plate. If no signal is detected in the wells containing the second agent, then the positive control has not worked and this suggests a problem with the assay conditions. If this occurs, negative results obtained in the wells lasting the second agent may be discounted.

In this embodiment of the invention, the agent capable of enhancing detection of cells may be a polyclonal activator such as an antibody to CD3 or a lectin such as phytohaemagglutinin (PHA) or convanavalin A (ConA). These activators may be useful in enhancing detection of activated T-cells.

The second agent capable of enhancing detection of one or more of the first, second and/or further analyte may act to potentiate specific secretion or production of the analyte in response to the first agent. The second agent may therefore, provide a co-stimulatory signal for production or secretion of or one or more of the analytes.

In the embodiment for detecting activated T-cells, the second agent may be an antibody or recombinant ligand to a co-stimulatory molecule such as CD28, inducible co-stimulatory (ICOS) molecule or CD40. Normal in vitro conditions provided in the assay may not promote optimal antigen presentation or the formation of cell-to-cell contacts, both of which are important for an immune response. The provision of a co-stimulatory signal in the assay, particularly where the second agent is immoblised on the solid surface may substitute for the signals normally provided in the cell-to-cell contacts and thus enhance the number of responding cells in a specific manner. For example, the use of immobilized anti-CD28 antibodies significantly enhances the specific response of T-cells to the antigens purified protein derivative (PPD) and tetanus toxin (TT).

Growth factors, such as IL-2 and/or IL-15, may also be used to potentiate secretion of an immunoreactive substance in response to a first agent. These growth factors act to potentiate specific immune responses providing the responding T-cells with further signals for activation. Other examples of suitable second agents are IL-4 which further potentiates the stimulation of IL-4 producing cells and IL-12 that may be used to promote the production of Th-1 cytokines such as interferon-γ (IFN-γ).

The second agent may alternatively enhance detection of the first, second and/or further analyte by inhibiting a signal which inhibits secretion of the analyte. For example, in the embodiment for the detection of T-cells, the second agent may be an antibody to a generally immunoinhibitory molecule such as IL-10 or TGF-β. Antibodies to generally immunoinhibitory molecules will "absorb" the immunoinhibitory molecules and preferably immobilise them on the well surface, thereby making the immunohibitory molecules less accessible to the potentially responding T-cells.

In another alternative, the second agent may act to inhibit a stimulatory signal in order to suppress spontaneous secretion of the first, second and/or further analyte. This may help to make the specific responses more easily revealed by improving the signal to noise ratio. For example Granzyme B and IFN-γ are both produced by natural killer (NK) cells as well as by T-cells. The second agent may suppress the spontaneous production of Granzyme B or IFN-γ from NK cells in order to aid detection of Granzyme B or IFN-γ from T-cells. Suitable second agents that act in this way include antibodies capable of neutralizing or blocking a stimulatory signal.

Extra-cellular matrix proteins such as fibronectin and laminin are further examples of agents capable of enhancing detection of an analyte by potentiating secretion of the substance in response to a stimulatory signal.

Extra-cellular matrix proteins are essential for the proper interaction of matrix-dependent cellular modulators, such as chemokines, with immune cells. Inclusion of extracellular matrix proteins may, therefore, be required to provide optimal conditions for stimulation.

In a method of the invention one, two, three or more, for example four or five, second agents capable of enhancing detection may be utilised. Where two or more such agents are used, the agents may act by the same or different mechanisms and may enhance the detection of the same or different analyte. For example, where the cells are T-cells, two constimulatory signals may be used to optimally detect both CD4 and CD8 responding cells. Here, the detection system is preferably based on more than one cytokine, such as IL-4 and IFN-γ which are usually produced by separate sets of T-cells.

In the embodiment of the invention for detecting virus infected cells, the second agent capable of enhancing detection of such cells is preferably an agent capable of activating virus replication. In the case of, for example HIV, the activator of viral replication may be a polyclonal activator such as anti-CD3 or PHA which both activate virus replication in T-cells.

Product

The invention also provides a product suitable for detecting the production by cells in a sample of one or more analyte, which product comprises a well comprising:
  (i) a first binding protein which specifically binds to a first analyte;
  (ii) optionally a second binding protein which specifically binds to a second analyte;

(iii) a first agent capable of inducting or inhibiting production of said first analyte and/or said second analyte; and
(iv) optionally a second agent which enhances detection of said first and/or second analyte, wherein said first binding protein and said optionally second binding protein are immobilized at one or more discrete location within said well and said first agent and optionally said second agent are immobilized within said well.

The product may be made by putting microdroplets (typically from 0.1 to 10 nl) of a solution containing the first binding protein or second binding protein on to the surface of the well. After allowing the binding proteins to immobilize on the surface, for example by overnight incubation at +4-8° C., excess antibodies are washed away and the surface may optionally be saturated with a blocking reagent such as bonine serum albumin (BSA).

Kits

The invention also provides a kit for carrying out a method of the invention, which kit comprises a product according to the invention, a means to detect binding of the first analyte and optionally the second and further analytes to the surface of the well.

The invention also provides a kit comprising (a) an assay plate comprising (i) a first binding protein which specifically binds to a first analyte; and (ii) optionally a second binding protein which specifically binds to a second anlayte wherein said first binding protein and optionally said second binding protein are immobilized at discrete locations within a well, typically such that introducing the cells into the well brings the cells into contact with both the first and second binding proteins; and (b) one or more of the following: cell culture medium, a means to separate mononuclear cells or T-cells from a blood sample; the first agent and the second agent.

The detection means typically comprises one or more antibody capable of binding to the first, second and/or further analyte or to the complex formed between the first binding protein and the first analyte, the second binding protein and the second analyte and/or the further binding protein and the further analyte. The antibody may be directly or indirectly labelled for detection.

The kit may additionally comprise medium for the cells and/or washing buffers to be used in the detection steps.

The kit may also comprise controls, such as positive or negative controls. The kit may also comprise a means to take a sample containing cells from a subject, such as a blood sample. The kit may comprise a means to separate mononuclear cells or T-cells from a blood sample.

Uses

The method of the invention may be used in research situations as well as in diagnostic applications. The method of the invention may be used in any known application of the ELISpot assay. The method of the invention may, in particular, be used in research to investigate specific immune responses, for example in vaccine studies. The method of the invention may be used in diagnostic assays aimed at detecting T-cell responses to various infectious diseases, allergens, tumour antigens or autoimmune targets.

The method of the invention has particular utility in drug screening, for example, in identifying anti-viral drugs and immunomodulatory agents.

The method of the invention may also be used to detect responses of a variety of isolated cells. For example, insulin producing islets isolated for transplantation could be monitored for insulin production and stress responses, dendritic cells isolated for immune therapy could be monitored for responsiveness and maturation markers and neuronal stem cells isolated for stroke therapy could be monitored for stress proteins and neuronal chemotactic factors.

The following Examples illustrate the invention.

Example 1

To test the specificity of the assay, a test assay plate (96-well ELISpot) was produced as shown in FIG. 1. Four different anti-cytokine catcher antibodies, αIFN-γ, αIL-2, αIL-10 and αIL-13 were spotted (4 nl/spot) onto PVDF plates in the pattern shown in FIG. 1.

The specificity of the system was then tested by the addition of purified cytokines. To the various wells were added 100 µl/well of a solution containing no cytokines, a solution containing 5 ng/ml of each of αIFN-γ, αIL-2, αIL-10 and αIL-13 or a solution containing 5 ng/ml of one of αIFN-γ, αIL-2, αIL-10 or αIL-13. Spots were developed by adding a mixture of biotinylated secondary antibodies (100 µl/well containing 1 µg/ml of antibodies to each cytokine). After washing away non-bound antibody, streptavidin conjugated with alkaline phosphatase (SA-ALP) was added. Finally, the spots were developed by use of an insoluble substrate to alkaline phosphatase, BCIP/NBT plus.

Example 2

PBMC (180 000/well) were cultured at 37° C. for 44 hours in a PVDF plate prepared as described in Example 1, in the presence of PPD (purified protein derivative from mycobacterium), pool of CD8-reactive viral peptides, flu-peptide (a single peptide from the influenza virus) or medium alone. After incubation the cells were washed away and biotin-conjugated detecting antibodies, SA-ALP and substrate were added as described in Example 1. An ELISpot was performed in parallel as a reference.

Due to a high spontaneous production of IL-10, mainly by monocytes, this cytokine is detected also in the control wells. A decreased production of IL-10 in the cultures with CD8 peptides and flu peptide may be dependent on a simultaneous production of one or more regulatory molecules suppressing IL-10 secretion (the same thing has previously been observed in ELISpot).

The lack of IL-2 and IL-13 spots reflects the lack of induction of these cytokines in this donor with the present antigens (also seen in ELISpot).

In the present setup each of the coating antibodies have been coated in 4 different spots. In a real test situation each antibody will more likely be coated only as one spot allowing the simultaneous analysis of a multitude of cytokines. The accumulation of cytokine in only one spot may also add to the sensitivity of the assay.

The invention claimed is:
1. A method for detecting the production of more than one analyte by cells in a sample, which method comprises:
(a) introducing a sample of cells into a well, wherein
(i) a first binding protein which specifically binds to a first analyte;
(ii) a second binding protein which specifically binds to a second analyte; and
(iii) optionally one or more further binding protein which specifically binds to one or more further analyte;
are each immobilized at one or more discrete locations on a solid surface within the well, wherein said discrete locations are spots;

(b) culturing said sample of cells under conditions suitable for:
   (i) release of said first analyte, said second analyte and optionally said one or more further analyte by said cells; and
   (ii) binding of said first analyte to said first binding protein, binding of said second analyte to said second binding protein and optionally binding of said one or more further analyte to said one or more further binding proteins; and
(c) determining whether or not said first analyte is bound to said first binding protein, whether or not said second analyte is bound to said second binding protein, and whether or not said one or more further analyte is bound to said one or more further binding proteins
thereby detecting production by a sample of cells of more than one analyte.

2. A method according to claim 1, wherein said spots are arranged as a grid.

3. A method according to claim 1, wherein one or more of said first binding protein, said second binding protein and said further binding protein is an antibody.

4. A method according to claim 1 wherein in step (b) cells are cultured in the presence of a first agent capable of inducing or inhibiting production of said first analyte, said second analyte and/or said one or more further analyte.

5. A method according to claim 4 wherein in step (b) cells are cultured in the presence of a second agent which enhances detection of one or more of said first analyte, said second analyte or said one or more further analyte.

6. A method according to claim 5, wherein said second agent:
   (i) potentiates production of said first analyte, said second analyte and/or said one or more further analyte in response to said first agent;
   (ii) inhibits a signal which suppresses production of said first analyte, said second analyte and/or said one or more further analyte; or
   (iii) inhibits a signal which stimulates spontaneous production of said first analyte, said second analyte and/or said one or more further analyte.

7. A method for detecting the production of more than one analyte by cells in a sample, which method comprises:
   (a) introducing a sample of cells into a well, wherein
      (i) a first binding protein which specifically binds to a first analyte;
      (ii) a second binding protein which specifically binds to a second analyte; and
      (iii) optionally one or more further binding protein which specifically binds to one or more further analyte;
   are each immobilized at one or more discrete locations on a solid surface within the well;
   (b) culturing said sample of cells under conditions suitable for:
      (i) release of said first analyte, said second analyte and optionally said one or more further analyte by said cells; and
      (ii) binding of said first analyte to said first binding protein, binding of said second analyte to said second binding protein and optionally binding of said one or more further analyte to said one or more further binding proteins,
   wherein the cells are cultured in the presence of a first agent capable of inducing or inhibiting production of said first analyte, said second analyte and/or said one or more further analyte and a second agent which enhances detection of one or more of said first analyte, said second analyte or said one or more further analyte, wherein said first agent and/or said second agent is immobilized in said well,
   (c) determining whether or not said first analyte is bound to said first binding protein, whether or not said second analyte is bound to said second binding protein, and whether or not said one or more further analyte is bound to said one or more further binding proteins,
thereby detecting production by a sample of cells of more than one analyte.

8. A method according to claim 7, wherein said first agent and/or said second agent is immobilized uniformly on base of said well.

9. A method according to claim 5, wherein said first agent and/or said second agent is added in solution.

10. A method according to claim 1 wherein said sample of cells comprises leukocytes.

11. A method according to claim 10, wherein one or more of said first analyte, said second analyte and said one or more further analyte is a cytokine.

12. A method according to claim 1, wherein said sample of cells comprises cancer cells, stem cells or isolated neural cells.

13. A method according to claim 1, wherein said sample of cells comprises cells that have been exposed to a infectious agent.

14. A method according to claim 13, wherein said infectious agent is a virus.

15. A method according to claim 14, wherein one or more of said first analyte, said second analyte and said one or more further analyte is a viral particle or protein.

16. A method for detecting the production of one or more analytes by cells in a sample, which method comprises:
   (a) introducing a sample of cells into a well, wherein
      (i) a first binding protein which specifically binds to a first analyte; and
      (ii) optionally a second binding protein which specifically binds to a second analyte;
   are each immobilized in separate spots arrayed on a solid surface within the well;
   (b) culturing said sample of cells under conditions suitable for:
      (i) release of said first analyte and optionally said second analyte by said cells; and
      (ii) binding of said first analyte to said first binding protein and optionally binding of said second analyte to said second binding protein; and
   (c) determining whether or not said first analyte is bound to said first binding protein and whether or not said second analyte is bound to said second binding protein,
thereby detecting production by a sample of cells of one or more analyte.

17. A method for detecting the production of more than one analyte by cells in a sample, which method comprises:
   (a) introducing a sample of cells into a well, wherein
      (i) a first binding protein which specifically binds to a first analyte;
      (ii) a second binding protein which specifically binds to a second analyte; and
      (iii) optionally one or more further binding protein which specifically binds to one or more further analyte;
   are each immobilized at one or more discrete locations on a solid surface within the well, where the discrete locations are spots;

(b) culturing said sample of cells under conditions suitable for:
- (i) release of said first analyte, said second analyte and optionally said one or more further analyte by said cells; and
- (ii) binding of said first analyte to said first binding protein, binding of said second analyte to said second binding protein and optionally binding of said one or more further analyte to said one or more further binding protein; and (c) determining whether or not said first analyte is bound to said first binding protein, whether or not said second analyte is bound to said second binding protein, and whether or not said one or more further analyte is bound to said one or more further binding protein, thereby detecting production by a sample of cells of more than one analyte.

18. A method for detecting the production of more than one analyte by cells in a sample, which method comprises:

(a) introducing a sample of cells into a well, wherein
- (i) a first binding protein which specifically binds to a first analyte;
- (ii) a second binding protein which specifically binds to a second analyte; and
- (iii) optionally one or more further binding protein which specifically binds to one or more further analyte;

are each immobilized at one or more discrete locations on a solid surface within the well;

(b) culturing said sample of cells under conditions suitable for:
- (i) release of said first analyte, said second analyte and optionally said one or more further analyte by said cells; and
- (ii) binding of said first analyte to said first binding protein, binding of said second analyte to said second binding protein and optionally binding of said one or more further analyte to said one or more further binding protein;

wherein said cells are cultured in the presence of a first agent capable of inducing or inhibiting production of said first analyte, said second analyte and/or said one or more further analyte and a second agent which enhances detection of one or more of said first analyte, said second analyte or said one or more further analyte, wherein said first agent and/or said second agent are immobilized at one or more discrete locations in said well, and (c) determining whether or not said first analyte is bound to said first binding protein, whether or not said second analyte is bound to said second binding protein, and whether or not said one or more further analyte is bound to said one or more further binding protein, thereby detecting production by a sample of cells of more than one analyte.

* * * * *

UNITED STATES PATENT AND TRADEMARK OFFICE
CERTIFICATE OF CORRECTION

PATENT NO. : 8,617,808 B2  Page 1 of 1
APPLICATION NO. : 11/587350
DATED : December 31, 2013
INVENTOR(S) : Braesch-Andersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this
Twenty-second Day of September, 2015

Michelle K. Lee
*Director of the United States Patent and Trademark Office*